US005515159A

United States Patent [19]
Sites et al.

[11] Patent Number: 5,515,159
[45] Date of Patent: May 7, 1996

[54] PACKAGE SEAL INSPECTION SYSTEM

[75] Inventors: Peter W. Sites, Knoxville; Bernard A. Roche, Farragut; Creed F. Jones, III; James C. Griner, both of Knoxville, all of Tenn.

[73] Assignee: Westinghouse Electric Corporation, Pittsburgh, Pa.

[21] Appl. No.: 386,404

[22] Filed: Feb. 10, 1995

[51] Int. Cl.$^6$ .................................................. G01N 21/17
[52] U.S. Cl. ........................................... 356/237; 356/239
[58] Field of Search .................................. 356/237, 239, 356/240, 376, 394; 382/141; 348/131

[56] References Cited

U.S. PATENT DOCUMENTS

| 4,220,966 | 9/1980 | Montone | 356/239 |
| 5,249,034 | 9/1993 | Minato | 356/237 |

FOREIGN PATENT DOCUMENTS

| 1-209307 | 8/1989 | Japan | 356/239 |

Primary Examiner—Richard A. Rosenberger

[57] ABSTRACT

On-line inspection of opaque, translucent and transparent elastomer sealed flexible and semi-rigid package seals is provided. In the case of highly reflective opaque seals of various elastomers and colors, low incident angle structured side lighting is used to locate and define the seal and highlight defects within the sealed area. For transparent i.e. highly light transmissive seals, not only is the low incident structured side lighting utilized to define the seal area, but back lighting of the package and seal is provided in order to then locate and classify defects within the seal boundaries. Multiple video images of portions of the area containing the seal and portions of the remaining lidstock are generated by CCD type cameras in response to one or more sensors which detect the presence and proper positioning of the package moving along a conveyor for image acquisition. The images generated are fed to one or more image processors which perform a series of stored program operations which determines if the package is accepted, possibly accepted, or rejected based upon the quality of the seal area and the presence of any defects in the seal boundaries.

30 Claims, 7 Drawing Sheets

PACKAGE SEAL INSPECTION SYSTEM

BACKGROUND OF THE INVENTION

1. Field of the Invention

This invention relates generally to vision systems for inspecting the integrity of seals on packaged goods and more particularly to an on-line machine vision system for inspecting the integrity of package seals for packages including elastomer seals.

2. Description of the Prior Art

Machine vision systems for inspecting the seals of packages containing various types of products moving at a relatively rapid rate along a production line are generally known and typically involve the use of one or more video cameras which are located at an inspection station where the packages are viewed as they pass along a conveyor. Images are generated of the packages which are then analyzed in order to determine the existence of any defects, for example, in the seal between a container and the lid affixed thereto.

Attempts to implement machine vision solutions seldom fail for lack of ability to perform the requisite analyses, but rather it is the failure to adequately capture images that contain all of the information necessary for performance of these analyses. This is due, for example, to incorrect sensor selection, improper optics, poor lighting, lack of attention to part positioning and/or materials handling problems and various other matters that can cause the system to acquire inadequate images and hence fail to operate as intended.

SUMMARY

Accordingly, it is an object of the present invention to provide an improvement in on-line machine vision systems for performing inspection of package seals.

It is another object of the invention to provide an on-line machine vision system for performing quality inspection of opaque, translucent, and transparent elastomer sealed flexible and semi-rigid package seals.

It is still another object of the invention to provide an improvement in the lighting utilized in an on-line machine vision inspection of package seals.

It is a further object of the invention to provide an on-line machine vision system for performing an inspection of a package seal for continuity, location and type of defect.

It is yet another object of the invention to provide an on-line machine vision system which can continuously monitor system operation and when necessary transmit inspection information to a host system for archiving and statistical analysis.

Briefly, the foregoing and other objects are achieved by apparatus and a method implemented thereby for performing on-line inspection of opaque, translucent and transparent elastomer sealed flexible and semi-rigid package seals. In the case of highly reflective opaque seals of various elastomers and colors, low incident angle e.g. 5°–15°, structured side lighting is used to locate and define the seal and highlight defects within the sealed area. Actual angle of incidence and intensity are application dependent, however, and thus may be tailored to the specific application intended. The structured light is generated by a plurality of low incident angle light sources located substantially perpendicular to a major axis of straight or substantially straight sections of the seal and a plurality of structured light sources located perpendicular to a chord of curved segments of the seal. For transparent i.e. highly light transmissive seals, not only is the low incident structured side lighting utilized to define the seal area, but uniform back lighting of the package and seal is provided in order to then locate and classify defects within the seal boundaries. Multiple video images of portions of the area containing the seal and portions of the remaining lidstock are generated by CCD type cameras in response to one or more sensors which detect the presence and proper positioning of the package moving along a conveyor for image acquisition. The images generated are fed to one or more image processors which perform a series of stored program operations which, among other things, define the straight and curved portions of the sealed area, the edges of the actual sealed area, and the actual width of the sealed area. The actual width is compared to a prescribed minimum value, then the package is (a) accepted, (b) possibly accepted, or (c) rejected. Unacceptable packages or possibly acceptable packages are diverted from the inspection station by diverter assemblies for further inspection. If the seal is acceptable, the images are next processed to detect the presence or absence of flaw candidates such as channel defects, cluster defects, or incomplete seals. Each flaw candidate is then subjected to further analysis for locating any flaws relative to their location on the package and determines the type and severity of each defect. The package is then again either (a) accepted or (b) rejected.

BRIEF DESCRIPTION OF THE DRAWINGS

This invention will be more readily understood when considered together with the accompanying drawings wherein.

DETAILED DESCRIPTION OF THE INVENTION

This invention discloses, among other things, a means to limit human inspection of elastomeric, heat and pressure sealed flexible and semi-rigid package seals while performing automatic machine vision inspection of package seals on-line at full production rates. The system to be described herein separates packages into three seal quality categories:

(a) acceptable; (b) possibly acceptable; and (c) not acceptable. "Acceptable" packages are directly shipped to customers. "Possibly acceptable" packages are diverted to a holding area for further inspection by other machines or involves human inspection. "Not-acceptable" packages are diverted to a reject area for possible recovery of usable product.

All the seals to be considered for inspection by this invention are considered to be reflective. Some are opaque and others are translucent, while still others are transparent. In all instances, the heat and pressure applied in fabricating the seal between the package and lidstock creates a coining effect that is visible as to its boundaries and defects only under proper lighting conditions.

Figure 1:
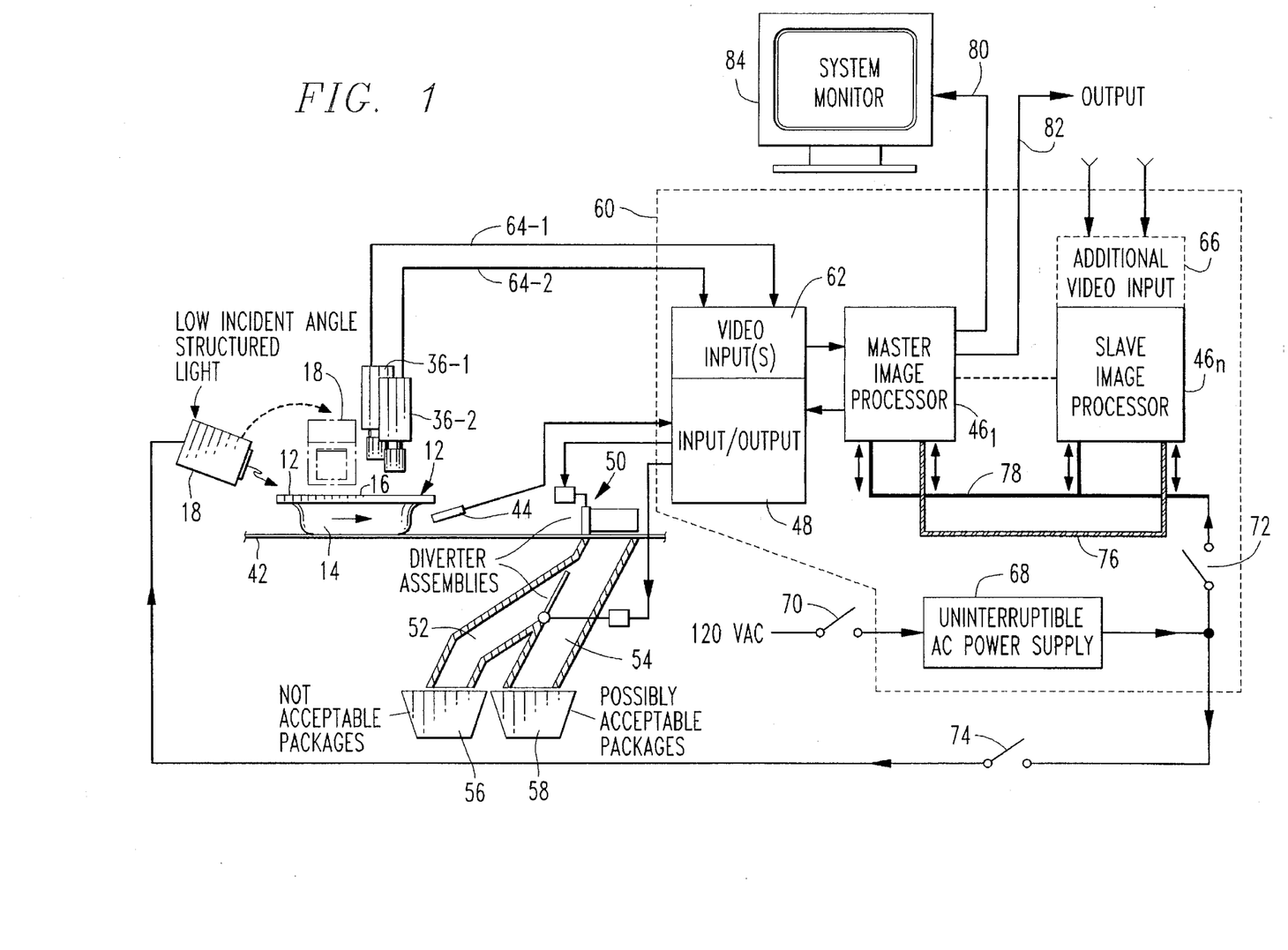
FIG. 1 is a system block diagram illustrative of one preferred embodiment of the subject invention.
Figure 3A:
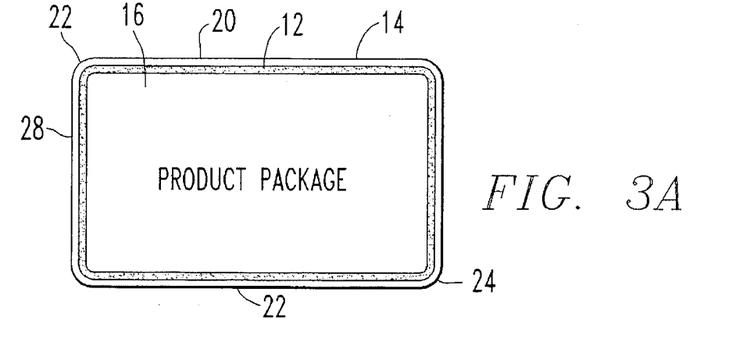
FIGS. 3A and 3B are plan and side elevational views, respectively, of a typical product package including an elastomer package seal.
Figure 3B:
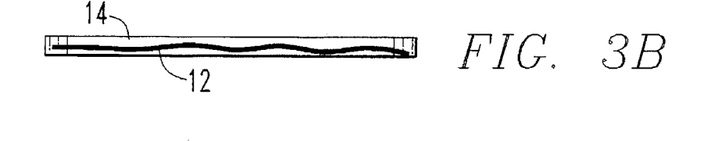

This now leads to a consideration of the various embodiments of the invention. Referring now to the drawings wherein like reference numerals refer to like components throughout, the embodiment shown in FIG. 1 depicts one station of one or more sequential inspection stations where highly reflective opaque seals 12 (FIG. 3A) located on the outer edge of a package 14 containing a product which is to be vended, not shown, and covered by lidstock 16 are inspected. The side view of FIG. 3B is indicative of a perimeter seal 12 of a flexible package 14. Semi-rigid packaging such as the package 14 shown, for example, in FIG. 4 has a relatively smooth, substantially level contour seal 12.

Figure 4:
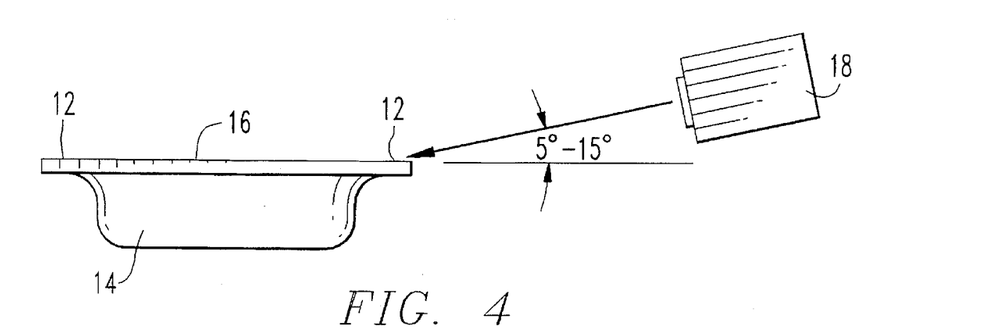
FIG. 4 is a front elevational view of a package under inspection and are receiving incident light from a structured light source from the side at a relatively low incident angle.

The configuration of FIG. 1 is utilized for highly reflective opaque seals of various elastomers and colors. In this embodiment, low incident angle structured light having a well defined beam is projected towards the top surface of the seal 12 and the outer edge of the package 14 at a relatively shallow angle (5°–15°) relative to the plane of the seal as shown in FIG. 4. Reference numeral 18 designates a structured incident light source of between 100 and 150 ft. candles. It should be noted, however, that the incident angle, intensity and shape of the beam is application dependent and thus may be varied to meet the specific task intended.

Figure 2:
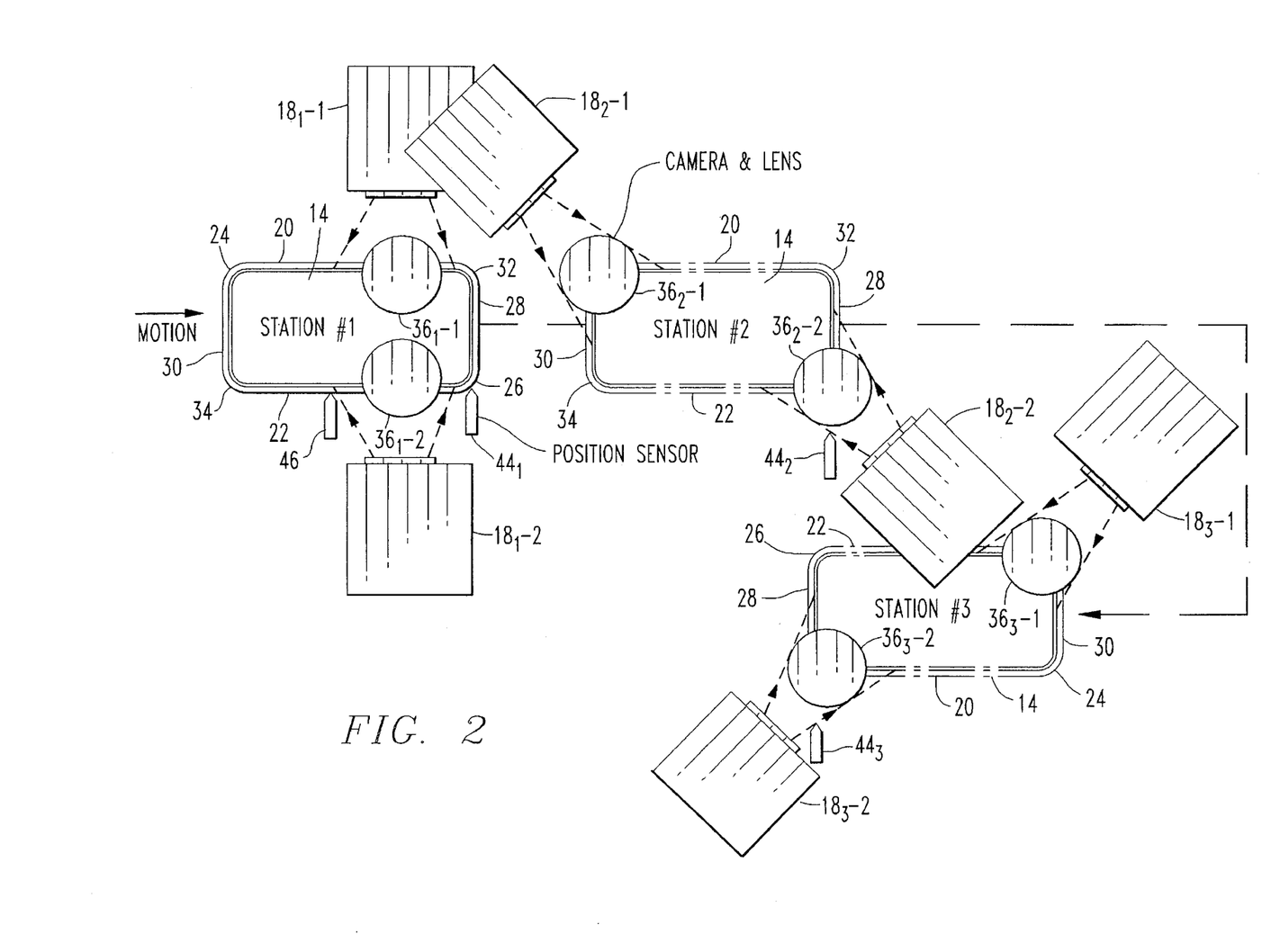
FIG. 2 is a schematic illustration of a multi-station inspection system for the embodiment shown in FIG. 1 including two image cameras and two low incident angle side lighting sources at each station.

Referring now to FIG. 2, in order to inspect the seal 12 completely around the perimeter of the package 14, three pairs of structured light sources $18_{1-1}$, $18_{1-2}$; $18_{2-1}$, $18_{2-2}$; and $18_{3-1}$ and $18_{3-2}$ are provided at three separate stations. Station number 1 is used for illuminating the long sides 20 and 22 of the package 12, the second for illuminating the rear left corner 24 and the forward right corner 26 as well as one half of the front and rear sides 28 and 30, and the third for illuminating the opposite diagonal corners, i.e. left front corner 32 and right rear corner 34 and the other half of the front and rear side 28 and 30. Such an arrangement, however, can be changed and/or modified depending on the specific application.

Associated with each low incident angle light source $18_1$-1, $18_1$-2, ... $18_3$-1, $18_3$-2 is an overhead charge couple device (CCD) camera $36_1$-1, $36_1$-2, $36_2$-1, $36_2$-2, $36_3$-1 and $36_3$-2, which respectively operate to grab or acquire image information as shown in FIG. 4. Image information may be front and rear half frame (field) images as images $38_F$, $38_R$, $40_F$, $40_R$ when interlaced cameras are used, full frame image when frame transfer cameras are used, or may be acquired using linear array (line scan) cameras, or variations thereof, such as time delay and integration cameras. If field acquisition type cameras are used, field acquisition takes place approximately 16ms displaced in time during which a package 14, moving on a conveyor 42 such as shown in FIG. 1 and traveling 100 feet per minute, moves 0.027 feet. If frame transfer or linear array cameras are used, object displacement is not of any concern.

Further as shown in FIG. 2, package front edge position sensors $44_1$, $44_2$ and $44_3$ are located at the three inspection stations for determining when a package 14 is in the appropriate position for acquiring one or more images by the respective pairs of cameras $36_1$-1, $36_1$-2, $36_2$-1, $36_2$-2; and $36_2$-1, $36_3$-2. An additional sensor 46 is located at the first station behind the front edge position sensor $44_1$ for detecting when a particular package 14 is leaving the first station. The number of sensors 44, 46, moreover, is not necessarily limited to the number shown, but is application dependent, and is therefore dependent upon the particular configuration desired. The same may be said with respect to the number of light sources 18 and CCD cameras 36.

Figure 6:
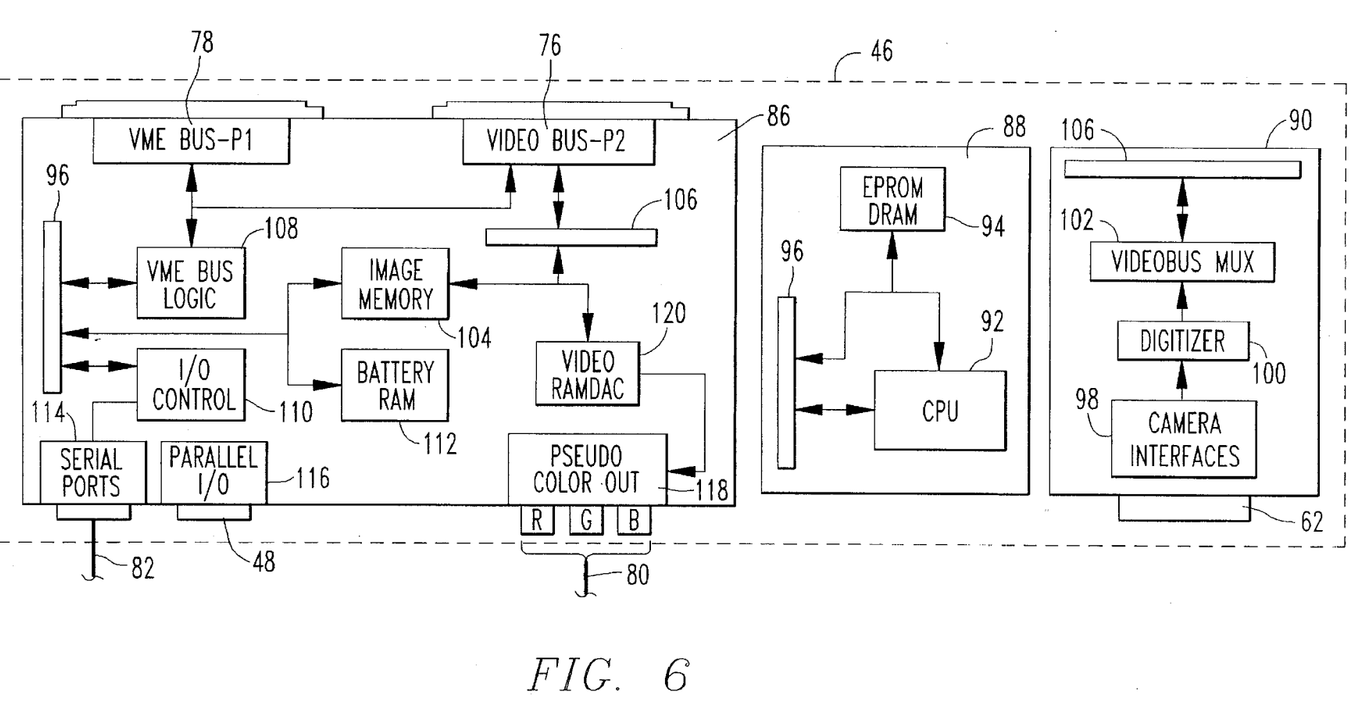
FIG. 6 is an electrical block diagram depicting the major components of an image processor utilized in the subject invention.

The actual number of images acquired at each location and the number of locations necessary to image the entire area of a package seal 12 again is application dependent. However, image processing begins as soon as an image is acquired by at least one system image processor 46, the details of which are shown in FIG. 6.

In FIG. 1, the embodiment for inspecting an opaque seal 12 includes a master image processor $46_1$ and a plurality of slave image processors, one of which is shown by reference numeral $46_n$. Thus at any given time, the system may be acquiring an image or images, processing an image or images, making decisions based upon the results of the image processing and analysis, and outputting signals from the master image processor $46_1$ through an input/output interface 48 to diverter mechanisms, for example, a pusher type diverter assembly 50 located alongside the conveyor 42 and a door type of diverter assembly associated with the pair of chutes 52 and 54 which feed initially rejected packages 14 into one or two containers 56 and 58 for receiving "non-acceptable" packages and "possibly acceptable" packages, respectively. The input/output interface 48 couples the package sensors $44_1$, $44_2$, $44_3$ and 46 to the master image processor $46_1$.

Reference numeral 60 denotes a system cabinet for housing the image processors $46_1$ ... $46_n$ in addition to the input/output interface 48 and a video input interface 62 which couples the video inputs from one pair of cameras 36-1 and 36-2 to the master image processor $46_1$ via electrical cables 64-1 and 64-2. Further, as shown in FIG. 1, each slave image processor, for example processor $46_n$, includes a video input interface 66 which would be coupled to a respective pair of cameras 36, not shown, but which would be, for example, another pair of cameras for one of the other stations shown in FIG. 2.

The system cabinet 60, moreover, houses an uninterruptible AC power supply unit which is coupled to a 120VAC source through a circuit breaker type switch 70. The output of the power supply unit 68 comprises, for example, a clean, regulated, uninterruptible 120 VAC, that is not subject to transient interruptions or surges, thereby protecting electronic components from damage. This supply voltage is applied through circuit breaker switch 72 to various transformer type power supplies, not shown, where voltages are reduced to more appropriate levels, e.g. + or −5 volts DC, and to 120 VAC devices, such as lighting systems, through circuit breaker switch 74. The master image processor $46_1$ and the slave image processor(s) $46_n$ are interconnected by means of a high speed video bus 76 and a bus 78, the latter being known in the industry as a VME bus. The master image processor $46_1$, in addition to sensing the state of the seal 12 at one of the inspection stations, generates output signals on cable leads 80 and 82 for indicating the inspection results on a video monitor 84 and for providing a communication interface to a host system, not shown, which exercises overall control of the system.

Referring now to FIG. 6, each of the image processors $46_1$ and $46_n$ comprise identical complete stand-alone modules which can operate either as a VME bus master or slave device. Each image processor is configured to include a standard VME mother board 86 and two piggy-back modules 88 and 90 which might be termed a CPU module and a video module, respectively. The CPU module 88 contains a CPU 92, e.g. a Motorola 68040 microprocessor, and an EPROM memory 94 comprising a DRAM having up to 8M bytes of memory. The CPU 92 and the memory 94 couple to the mother board 86 by way of a multi-pin connector 96. The video module 90 includes a camera interface(s) 98 which is located between the video interface 62 shown in FIG. 1 and a digitizer 100, typically an A/D converter for digitizing the input video information. The output of the digitizer 100 is then fed to a multiplexed video data bus 102 which is then coupled to an image memory 104 via connector 106.

The mother board additionally includes a VME bus logic section 108 and an input/output control section 110. The bus logic 108 connects the VME bus 78 and the video bus 76 to the internal connector 96, while the I/O control element 110 connects serial ports 114 and parallel I/O ports 116 to cable 82 (FIG. 1) and to the input/output interface 48. Finally, a series of pseudo color output ports 118 couple the processed video from a video RAMDAC 120 to the system monitor cable 82.

Figure 5:
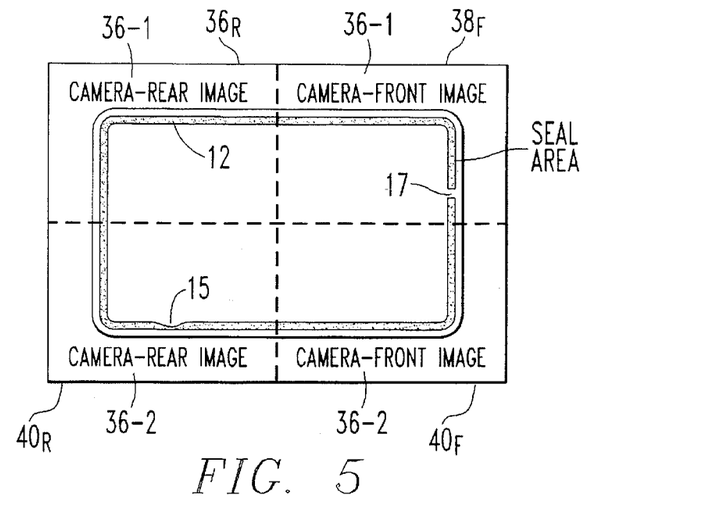
FIG. 5 is illustrative of four images generated for analysis by a pair of video cameras at each inspection station.
Figure 7:
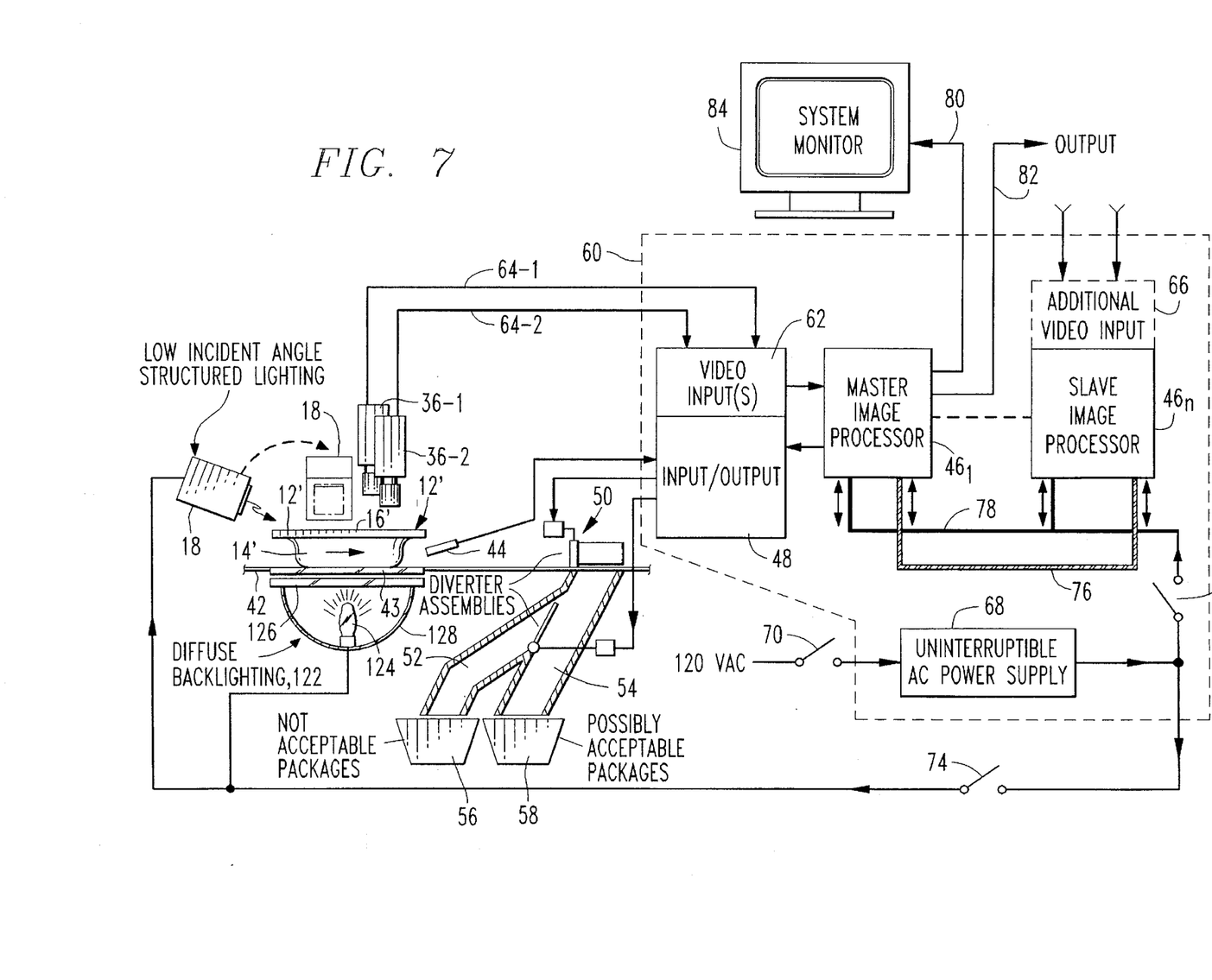
FIG. 7 is a system block diagram illustrative of another preferred embodiment of the invention.

Before considering further operational details of this invention, the embodiments disclosed in Figures 7 and 8 will first be explained. Whereas the first embodiment depicted in FIGS. 1 and 2 is utilized to locate and define the true area of highly reflective opaque seals 12 of various elastomers and colors and thereafter highlight and classify any defects, such as the defects consisting of a narrowed sealed width region 15 or a discontinuity defect 17 such as shown in FIG. 5 using low incident angle structured incident lighting, the embodiment shown in FIG. 7 is designed to inspect fully transparent or nearly transparent and, therefore, highly light transmissive seals 12' formed between a package 14' and lidstock 16' using two types of lighting. The embodiment of FIG. 7 is substantially the same as the first embodiment shown in FIG. 1, but now additionally includes diffuse backlighting of the seal 12 as well as low incident angle side lighting. The backlighting is provided by an assembly 122 including a light transmissive diffuser member 124 and a relatively low intensity light source 126 having an intensity of between 5 and 25 ft. candles together with a reflector 128 which is located beneath the conveyor 42. Again the specific intensity is application dependent and thus may be varied depending on the specific application. The conveyor 42 now includes transparent or light transmissive sections 43 the size of the package 14' for the passage of light upwardly therethrough. In operation, the low incident angle side lighting is utilized, as before, to define the actual area of the seal 12'; however, the backlighting is now used to locate and classify defects 15 and 17, for example, as shown in FIG. 5, within the seal boundaries.

Figure 8:
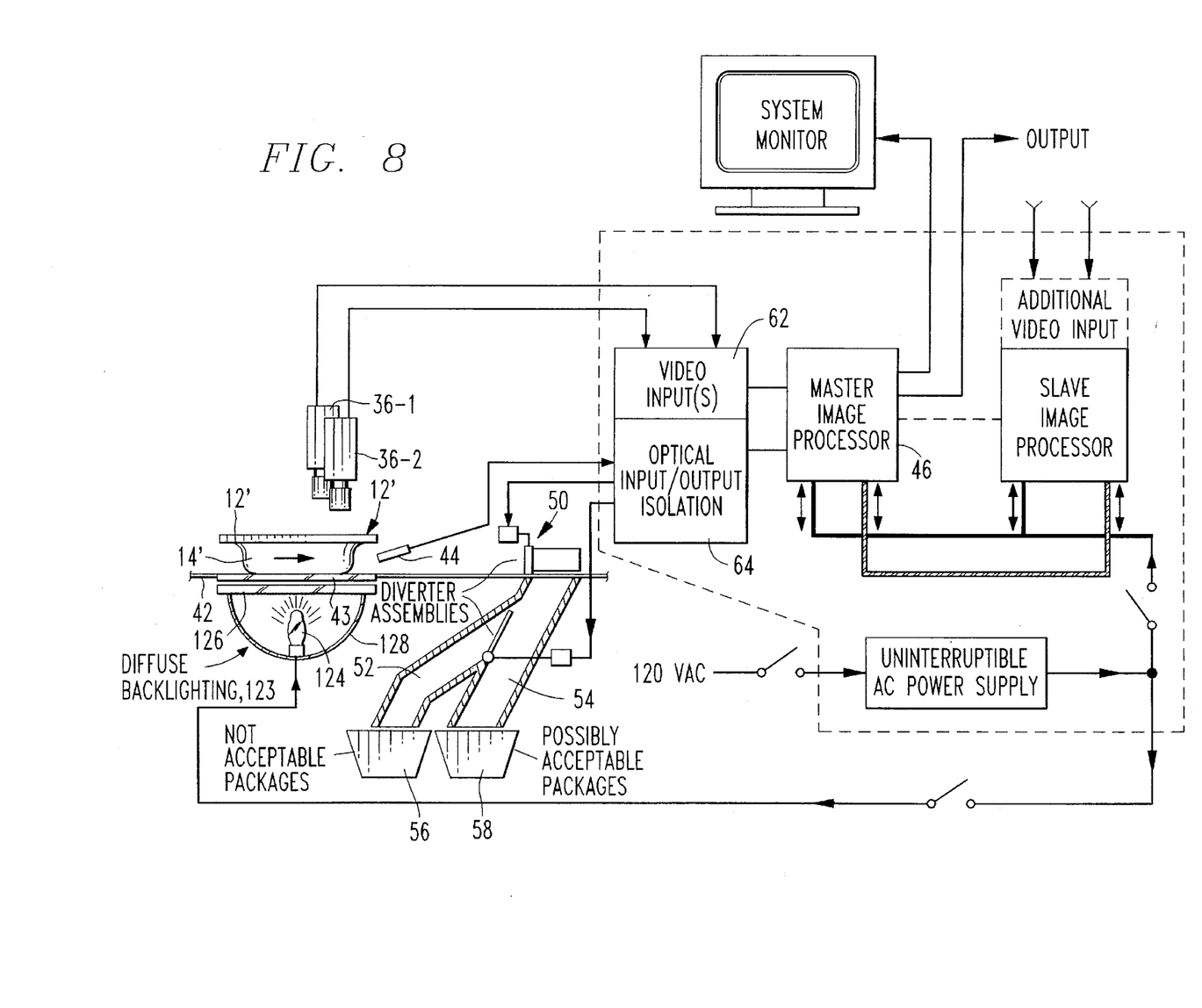
FIG. 8 is a system block diagram illustrative of still another preferred embodiment of the subject invention.

As to the embodiment shown in FIG. 8, where markings are previously placed on the package 14' to define the seal area for substantially transparent and highly light transmissive seals 12', a system having only diffused backlighting need be used since the only task now is to locate and classify defects as in FIG. 7. In FIG. 8, the low incident angle structured lighting system is eliminated and only a diffused backlighting system 123 including the diffuser 124, the electric lamp 126 and reflector 128 are positioned below the conveyor 42 which again requires transparent sections 43 so that uniform backlighting can be transmitted through the package 14' and seal 12' to, for example, cameras 36-1 and 36-2.

Figure 9:
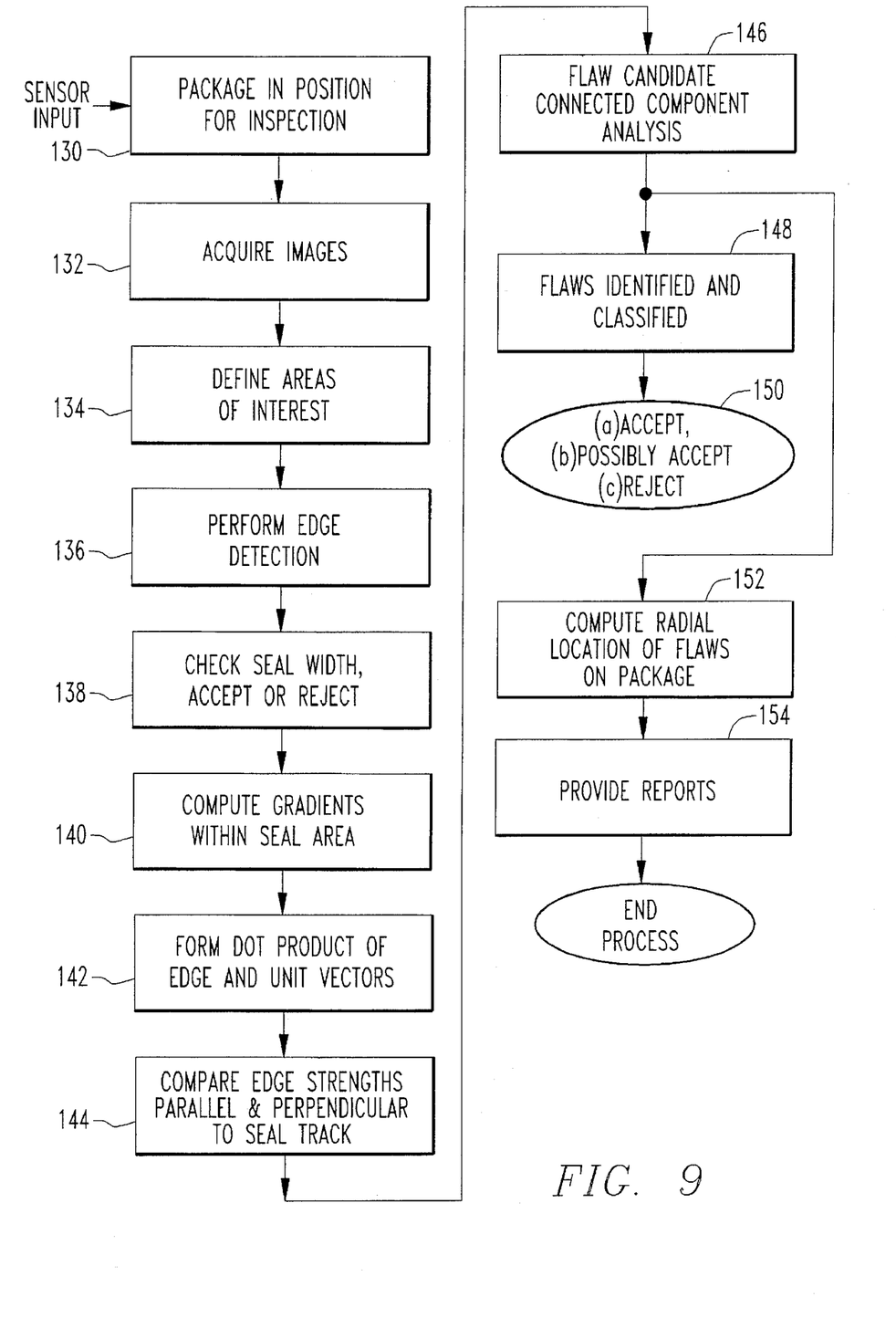
FIG. 9 is a flow chart illustrative of the computer software for implementing the algorithms for carrying the inspection of seals in accordance with the subject invention.

Considering now the flow chart of FIG. 9, depending upon which of the embodiments are utilized, detection of seals 12 or 12' is performed by first positioning a package 14 or 14' for inspection per step 130 and then acquiring images of portions of the lidstock which contains the seal and some portions of the remaining lidstock per step 132. Areas of interest are next defined in both the straight and curved portions of the seal and the edges of the seal are then defined through application of a series of linear scans of the images generated by pairs of CCD cameras which produce pairs of edge points that define the actual inner and outer edges of the seal. This is noted in steps 134 and 136.

This is followed by comparing the actual width of the seal to a prescribed minimum value as indicated by step 138 whereupon the seal 12 or 12' and accordingly the package 14 or 14' is accepted or rejected. If a defect as shown by reference numeral 15 in FIG. 5 is detected, the package would be rejected.

If accepted other flaws are detected next by computing the gradient of each pixel of the image generated within actual boundaries of the seal, keeping the vector components separated. This is indicated by step 140. Next, dot products of the edge vectors and a unit vector parallel to the actual seal are generated as shown by step 142.

This is followed by step 144 where a comparison is made of the magnitude of the edge strength in directions parallel and perpendicular to the seal track to reveal the presence or absence of flaw candidates such as channel defects, cluster defects, or incomplete seals.

Each flaw candidate is then subjected to a connected component analysis as shown by steps 146 and 148 followed by a determination step 150 of accepting, possibly accepting, or rejecting the package. Then further analysis is carried out which includes the step 153 of locating the flaw relative to its location on the package and providing a report per step 154 which is generated in accordance with the output of the master image processor.

All images acquired by the pairs of cameras 36-1 and 36-2 at an inspection station are processed in the same fashion as follows. Areas of interest appropriate to the geometry of the seal are defined in each acquired image. The areas of interest are rectangular, with one or more such areas positioned over and with their major axes parallel to the straight sections of the seal, and one positioned approximately at the mid-point of any curved areas of the seal as shown, for example, in the multi-station configuration of FIG. 2.

Within each area of interest, a number of search vectors are defined perpendicular to the edges of the seal area. Along each search vector, the gradient is computed according to the following equation:

$$\text{gradient} = \text{abs}(P_{i-1,j+1} + 2*P_{ij} + 1 + P_{i+1,j+1}) - \quad (1)$$

$$(P_{i-1,j-1} + 2*P_{i,j-1} + P_{i+1,j-1}) +$$

$$\text{abs}(P_{i-1,j+1} + 2*P_{i-1,j} + P_{i-1,j-1}) - (P_{i+1,j+1} + 2*P_{i+1,j}P_{i+1,j-1})$$

where: P is the pixel of interest within a 3×3 pixel matrix lying centered along the search vector, Pij is the pixel at the center of the above mentioned pixel matrix; and, the remainder are pixel locations relative to $P_{ij}$.

Potential edge points which are a predetermined distance apart, based on the expected geometry of the seal, are identified by noting those points where the calculated gradient magnitude meets or exceeds an experimentally determined, for the particular system design, threshold value.

These points are identified as the edges of the seal area. This processing is repeated for each search vector in each area of interest. One point of each pair corresponds to the inside edge of the seal area while the other point corresponds to the outer edge.

Due to noise, glare, and other image artifacts, some points may be incorrectly located. In other words, the data is "noisy" but the noise is not normally distributed. To remove the effect of this noise on the precise definition of the seal area, the points are chosen in sets of three to perform a curve fit. If the results of any curve fit operation are not compatible with the rest, those points are discarded. However, one point is chosen from each area of interest present in the image. These points are used to mathematically derive a curve consisting of a line segment for the side of the seal area and an ellipse with a specified eccentricity for the end area of the package. The eccentricity is determined by the geometry of the package and the imaging hardware, and is fixed at system setup time.

By repeating this process for all of the sets of points present in the areas of interest, a number of curves are obtained. These curves are defined in terms of the ellipse center point and diameter, and the slope and intercept of the line segment. The center points and line slopes are examined to determine the "clustering". If the standard deviation of any of these quantities exceeds a value equal to the total error that would be introduced by allowing any single point on a curve to deviate from the curve by an amount equal to one-fourth the seal width, it is concluded that one or more of the curves is in error.

An iterative process is carried out which determines which curve is most in error. This curve is removed, and the process is repeated until the standard deviation falls within predetermined limits, indicating significant agreement between the remaining curves. Once the curves are combined in this fashion, the remaining data is combined to produce the final overall curve fit for the seal area edge.

When curves are obtained for the inner and outer seal area edges, the curves are checked mathematically to see if the edges they define are closer together than a specified minimum distance, which varies by the particular application intended. This indicates insufficient seal width to properly protect the package contents at that point, and the package is rejected. This fast check is done to detect gross errors in seal width without tracing the entire seal area and checking width at each point, which requires much more processing time.

Accordingly, the seal area consists of the area bounded by the inner and outer curves. Within this irregularly shaped region of interest, flaw enhancement and detection are next carried out. Because flaws tend to have strong visual components perpendicular to the major axis of the seal, while illumination artifacts and shadows generally lie parallel to the seal, it is desirable to emphasize intensity changes along the seal area. To do this, the gradient vector parallel to the seal track is computed at each point in the seal area. The process to perform this operation is governed by the following general mathematical procedure.

(1) At each point in the seal area, a unit vector parallel to the seal track is derived by computing the derivative of the seal curve equation;

(2) The gradient vector is approximated using a pair of 5×5 masks, one to calculate the horizontal component of the gradient and one for the vertical;

(3) The dot product of the gradient vector and the unit vector is formed at each pixel; this is equivalent to the magnitude of edge strength in the direction of the track.

If the unit vector is represented by U, the gradient vector by G, the edge mask matrices by Mx and My, and the image neighborhood of the pixel (ij) as I(ij), the resulting edge strength is:

$$e(i,j) = U(i,j) \cdot G(i,j) = Ux(i,j)*Gx + Uy(i,j)*Gy \quad (2)$$
$$= Ux(i,j)*(Mx*I(i,j)) + Uy(i,j)*(My*I(i,j))$$

(4) To examine this enhanced data for potential flaws, a number of gray-level and variance statistics are collected as the edge data is computed. Based on these overall statistics, a threshold for the edge data is selected and applied to the image; and (5) Connected component or "blob" analysis is performed in a well known manner to locate any significant areas of edge activity. If none are found, the seal area is free of anomalies and the package is deemed acceptable.

If any sizable areas of edge strength are found, it still must be determined whether they represent actual flaws or artifacts of some kind. To do this, a number of features are next calculated for each flaw candidate. They include: connection status (flaw connected to the inner edge, outer edge, or both), area, density or "darkness" aspect ratio, "stringiness", angle of orientation, and solidity or number of holes. If a flaw is connected to both edges, it is defined as a channel leak, and the package is rejected. Small flaws which are nearly circular and not connected to the edge, called star or cluster flaws, usually correspond to a contaminant trapped beneath the seal. Such a package is also rejected. Other types of flaw candidates, such as cuts, tears, or markings specific to a particular application, may also be defined and the system configured to locate, identify, and reject them.

For each application, the package perimeter is defined in some number of agreed sectors of arc as measured from the geometric center of the package. Defect locations relative to these defined sectors are computed using the information generated by the foregoing connected components analysis. Knowing the location of defects provides an aid to inspectors in determining and correcting the cause of the defect, so this information, along with other application-specific data, is reported by the system.

Thus what has been shown and described is an automatic machine vision inspection system for flexible and semi-rigid package seals comprised of opaque, translucent and transparent elastomeric material which is tolerant of position or internal variation, angular or skew variations, vibrations induced by conveyor motion, and variations in the angle of the sealed surface with respect to the system imaging cameras.

Having thus shown and described what is considered to be the preferred method and embodiments for implementing the subject invention, it is to be noted that the same has been made by way of illustration and not limitation. Accordingly, all modifications, alterations and changes coming within the spirit and scope of the invention are herein meant to be included.

We claim:

1. A system for inspecting flexible and semi-rigid package seals, comprising:

means for transporting a package including a seal to and from at least one inspection station;

means located to the side of said package and said seal at said inspection station for generating and directing light to the seal at a relatively low incident angle relative to a surface of the seal;

means located above the package at said inspection station for generating at least one image of the seal from the low incident angle light reflected therefrom;

image processor means coupled to the means for generating said at least one image for defining the boundaries of the seal, determining the existence of any deflects in the seal and thereafter generating an output signal indicative of the quality of the seal; and means responsive to said output signal for accepting or rejecting said package from the system depending on the quality of the seal.

2. A system according to claim 1 wherein said means for generating and directing light to the seal comprises at least one structured light source for generating a structured beam at a predetermined incident angle relative to said surface of the seal.

3. A system according to claim 2 wherein said surface of the seal comprises the top surface of the seal.

4. A system according to claim 3 wherein said structured light source comprises a light source having a predetermined intensity.

5. A system according to claim 4 wherein said at least one structured light source comprises a pair of structured light sources selectively located around the periphery of the package at said one inspection station for directing light therefrom to mutually different regions of the seal.

6. A system according to claim 5 wherein said means for generating said at least one image comprises a pair of cameras respectively located so as to generate an image of said mutually different regions of the seal.

7. A system according to claim 6 wherein said pair of cameras comprises video type cameras.

8. A system according to claim 7 wherein each of said video cameras acquire image video signals in separate interlaced fields, as full image frames, or in a linear array.

9. A system according to claim 8 wherein said image processor means includes means for digitizing said video signals and a microprocessor means operating in response to the digitized video signals generating said output signal.

10. A system according to claim 9 wherein said means for transporting comprises a production line conveyor.

11. A system according to claim 3 wherein said seal comprises a substantially transparent seal and a fully transparent seal.

12. A system according to claim 11 and additionally including means for backlighting said package and said seal.

13. A system according to claim 12 wherein said means for backlighting comprises a light source having a predetermined intensity.

14. A system according to claim 11 and wherein said image processor means additionally determines the location of said defects and the type and severity of said defects.

15. A system according to claim 2 wherein said seal comprises an opaque seal or a translucent seal.

16. A system for inspecting substantially transparent and fully transparent package seals, comprising:

means for transporting a package including a substantially transparent or a fully transparent seal to and from at least one inspection station;

structure light source means located to the side of said package and said seal at inspection station for generating and directing light to the seal at a predetermined relatively low incident angle relative to a surface of the seal;

means located beneath said package and said seal for backlighting at least said seal;

means located above the package at said inspection station for generating at least one image of the seal from reflected incident light from said structured light source means for generating and directing light at a low incident angle and said means for backlighting;

image processor means coupled to the means for generating said at least one image for defining the boundaries of the seal, determining the existence and location of defects in the seal as well as classifying the type and severity of said defects and thereafter generating an output signal indicative of the quality of the seal; and means responsive to said output signal for accepting or rejecting said package from the system depending on the quality of the seal.

17. A system according to claim 16 claim wherein said surface of the seal comprises the externally visible surface of the seal.

18. A system according to claim 17 wherein said structured light source means comprises a light source having a first predetermined intensity and wherein said means for backlighting comprises a light source having a second predetermined intensity.

19. A system according to claim 18 wherein said means for backlighting includes diffuser means located between said light source and said seal.

20. A system according to claim 17 wherein said structured light source means comprises a pair of structured light source selectively located around the periphery of the package at said one inspection station for detecting light therefrom to mutually different regions of the seal.

21. A system according to claim 20 wherein said means for generating said at least one image comprises a pair of video type cameras respectively located so as to generated an image of said mutually different regions of the seal.

22. A system according to claim 21 wherein each of said video cameras acquire image video signals in interlace fields, as full image frames, or in a linear array.

23. A system according to claim 22 wherein said image processor means includes means for digitizing said video signals and a microprocessor means operating in response to the digitized video signals for generating said output signal.

24. A system according to claim 23 said means for transporting comprises a production line conveyor.

25. A system for inspecting the seal area of substantially transparent and fully transparent package seals, comprising:

means for transporting a package including a substantially transparent and fully transparent seal, having a predetermined seal area, to and from at least one inspection station;

means located beneath said package and said seal for backlighting the seal area;

means located above the package at said inspection station for generating at least one image of the seal from the light incident thereon from the means for backlighting;

image processor means coupled to the means for generating said at least one image for determining the existence of any defects in the seal, the location of said defects, the type of severity of said defects and thereafter generating an output signal indicative of the quality of the seal; and means responsive to said output signal foe accepting or rejecting said package from the system depending on the quality of the seal.

26. A system according to claim 25 wherein said means for backlighting comprises a light source having a predetermined intensity.

27. A system according to claim 26 wherein said means for backlighting includes diffuser means located between said light source and said seal.

28. A system according to claim 26 wherein said means generating said at least one image comprises a pair of video cameras, each of said video cameras acquiring image video signals in separate interlaced field, as full frames, or in a linear array.

29. A system according to claim 28 wherein said image processor means includes means for digitizing said video signals and a microprocessor means operating in response to the digitized video signals for generating said output signal.

30. A system according to claim 25 wherein said means for transporting comprises a production line conveyor.

* * * * *